United States Patent
Ali et al.

(10) Patent No.: US 8,623,846 B2
(45) Date of Patent: Jan. 7, 2014

(54) DIAZENIUMDIOLATE CYCLOHEXYL DERIVATIVES

(75) Inventors: Amjad Ali, Freehold, NJ (US); Lin Yan, East Brunswick, NJ (US); Pei Huo, Millburn, NJ (US); Ravi Nargund, East Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/698,444

(22) PCT Filed: May 16, 2011

(86) PCT No.: PCT/US2011/036607
§ 371 (c)(1),
(2), (4) Date: Nov. 16, 2012

(87) PCT Pub. No.: WO2011/146371
PCT Pub. Date: Nov. 24, 2011

(65) Prior Publication Data
US 2013/0059823 A1 Mar. 7, 2013

Related U.S. Application Data

(60) Provisional application No. 61/347,042, filed on May 21, 2010.

(51) Int. Cl.
*A61K 31/655* (2006.01)
*C07C 245/02* (2006.01)
*C09B 44/02* (2006.01)

(52) U.S. Cl.
USPC .............................. 514/150; 534/556; 534/574

(58) Field of Classification Search
None
See application file for complete search history.

(56) References Cited

U.S. PATENT DOCUMENTS

| | | | |
|---|---|---|---|
| 5,614,656 A | 3/1997 | Toda | |
| 6,750,254 B2 | 6/2004 | Hrabie | |
| 7,348,319 B2 | 3/2008 | Hrabie | |
| 2005/0065194 A1 | 3/2005 | Shankar | |
| 2005/0137191 A1 | 6/2005 | Thatcher | |

FOREIGN PATENT DOCUMENTS

| | | |
|---|---|---|
| WO | 97/46521 A1 | 12/1997 |
| WO | 2007/144512 A2 | 6/2007 |
| WO | 2009/070241 A2 | 6/2009 |
| WO | WO 2009094242 * | 7/2009 |
| WO | 2009/103875 A | 8/2009 |

OTHER PUBLICATIONS

Saavedra et al. Journal of Organic Chemistry (1992), 57(23), 6134-8.*

* cited by examiner

*Primary Examiner* — Jason M Nolan
*Assistant Examiner* — Ana Z Muresan
(74) *Attorney, Agent, or Firm* — Richard S. Parr; Catherine D. Fitch

(57) ABSTRACT

A compound having the structure (I) or a pharmaceutically acceptable salt thereof, wherein $R^3$ is hydrogen, deuterium, —OH, —OC$_{1-6}$alkyl, or halogen; $R^8$ is hydrogen, deuterium, or C$_{1-6}$alkyl; $R^{11}$ and $R^{12}$ are independently hydrogen, —C$_{1-6}$alkyl, —OH, —OC$_{1-6}$alkyl, or halogen; $R^{13}$ and $R^{14}$ are independently —C$_{1-6}$alkyl, —(CH$_2$)$_{1-2}$OH, or —OC$_{1-6}$alkyl, or, together with the nitrogen atom to which they are attached, form a 4- to 7-membered heterocyclic ring containing one nitrogen atom and 0 or 1 oxygen atoms, wherein said ring is unsubstituted or mono-, di- or tri-substituted with halogen or —C$_{1-6}$alkyl; R15 is —C(O)OH, —C(O)OCH$_2$CH$_2$N$^+$CH$_3$)$_3$ wherein n is 0, 1 or 2, —C(O)NHCH(R$^{17}$)OR$^{16}$, or —C(O)NHCH(R$^{17}$)C(O)NHCH(R$^{18}$)C(O)OR$^{16}$; R$^{16}$ is hydrogen, C$_{1-6}$alkyl, or (CH$_2$)$_{1-2}$N$^+$R$^{19}$R$^{20}$R$^{21}$; $R^1, R^2, R^4, R^5, R^6, R^7, R^9, R^{10}, R^{17}, R^{18}, R^{19}, R^{20}$, and $R^{21}$ are independently hydrogen or —C$_{1-6}$alkyl; and stereoisomers thereof, and pharmaceutically acceptable salts thereof, and pharmaceutically acceptable salts of stereoisomers thereof.

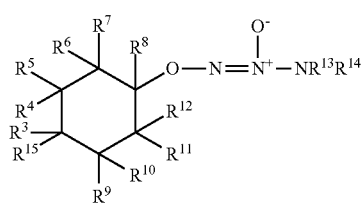

15 Claims, No Drawings

DIAZENIUMDIOLATE CYCLOHEXYL DERIVATIVES

BACKGROUND OF THE INVENTION

WO09103875 describes diazeniumdiolate dihydro indole derivatives of a specified formula for treating hypertension and cardiovascular disease. WO07144512 describes diazeniumdiolate tetrazole-biphenyl derivatives of a specified formula for treating hypertension and cardiovascular disease. US 2005137191 describes nitrate ester compounds, e.g., 1,2-dichloro-4-(2-methyl-butyldisulfanyl)-benzene, useful for preventing or mitigating tissue and/or cellular damage associated with aging, septic shock, ulcers, gastritis, ulcerative colitis and Crohn's disease. US 2005065194 describes use of an endothelial gene differentiation receptor modulator such as 1-(2-ethoxyphenyl)-3-(hydroxyphenylamino)-pyrrolidine-2,5-dione, to modulate receptor-mediated biological activity such as cell proliferation stimulated by lysophosphatidic acid leading to ovarian cancer and other forms of cancer, and to treat conditions such as cancer, cardiovascular disease, ischemia, and atherosclerosis. WO 9746521 describes aliphatic nitrate esters useful for treating neurological conditions, especially Parkinson's, Alzheimer's and Huntington's disease.

The present invention relates to novel diazeniumdiolate cyclohexyl derivatives, useful as antihypertensive agents.

SUMMARY OF THE INVENTION

The present invention includes diazeniumdiolate cyclohexyl derivatives, including various pharmaceutically acceptable salts and hydrates of these forms, and pharmaceutical formulations comprising the diazeniumdiolate cyclohexyl derivatives.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

The invention is a compound of formula I:

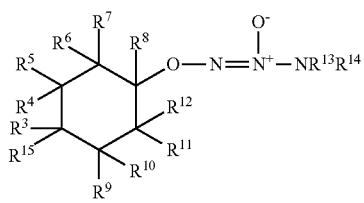

or a pharmaceutically acceptable salt thereof, wherein
$R^3$ is hydrogen, deuterium, —OH, —OC$_{1-6}$alkyl, or halogen;
$R^8$ is hydrogen, deuterium, or —C$_{1-6}$alkyl;
$R^{11}$ and $R^{12}$ are independently hydrogen, —C$_{1-6}$alkyl, —OH, —OC$_{1-6}$alkyl, or halogen;
$R^{13}$ and $R^{14}$ are independently —C$_{1-6}$alkyl, —(CH$_2$)$_{1-2}$OH, or —OC$_{1-6}$alkyl, or, together with the nitrogen atom to which they are attached, form a 4- to 7-membered heterocyclic ring containing one nitrogen atom and 0 or 1 oxygen atoms, wherein said ring is unsubstituted or mono-, di- or tri-substituted with halogen or —C$_{1-6}$alkyl;
$R^{15}$ is
—(CR$^1$R$^2$)$_n$C(O)OR$^{16}$, wherein n is 0, 1 or 2,
—C(O)NHCH(R$^{17}$)OR$^{16}$, or
—C(O)NHCH(R$^{17}$)C(O)NHCH(R$^{18}$)C(O)OR$^{16}$;
$R^{16}$ is hydrogen, —C$_{1-6}$alkyl, or —(CH$_2$)$_{1-2}$N$^+$R$^{19}$R$^{20}$R$^{21}$;
$R^1$, $R^2$, $R^4$, $R^5$, $R^6$, $R^7$, $R^9$, $R^{10}$, $R^{17}$, $R^{18}$, $R^{19}$, $R^{20}$, and $R^{21}$ are independently hydrogen or —C$_{1-6}$alkyl;
and stereoisomers thereof, and pharmaceutically acceptable salts thereof, and pharmaceutically acceptable salts of stereoisomers thereof.

In one embodiment, $R^1$ and $R^2$ are hydrogen.
In another embodiment, $R^3$ is hydrogen or deuterium.
In another embodiment, $R^5$ is hydrogen or methyl.
In another embodiment, $R^4$, $R^6$, $R^7$, $R^8$, $R^9$, and $R^{10}$ are hydrogen.
In another embodiment, $R^{13}$ is —CH$_3$, —CH$_2$CH$_3$, —CH$_2$CH$_2$CH$_2$CH$_3$, or —CH$_2$CH$_2$OH.
In another embodiment, $R^{14}$ is —CH(CH$_3$)$_2$, —CH$_2$CH$_3$, or —C(CH$_3$)$_3$.
In another embodiment, $R^{15}$ is —C(O)OH.
In another embodiment, $R^{15}$ is —C(O)OCH$_2$CH$_2$N$^+$(CH$_3$)$_3$.
In another embodiment, $R^{15}$ is —C(O)NHCH(CH(CH$_3$)$_2$)OR$^{16}$, or —C(O)NHCH(CH(CH$_3$)$_2$)C(O)NHCH(CH(CH$_3$)$_2$)C(O)OR$^{16}$, and $R^{16}$ is hydrogen or —CH$_3$.

In another embodiment, the compound is
Cis-4-({[(1Z)-2-tert-butyl-2-ethyl-1-oxido-1λ$^5$-diazan-1-ylidene]amino}oxy)-cyclohexanecarboxylic acid (Ex 1),
Trans-4-({[(1Z)-2-tert-butyl-2-ethyl-1-oxido-1λ$^5$-diazan-1-ylidene]amino}oxy)-cyclohexanecarboxylic acid (Ex 2),
Cis-4-({[(1Z)-2-tert-butyl-2-methyl-1-oxido-1λ$^5$-diazan-1-ylidene]amino}oxy)-cyclohexanecarboxylic acid (Ex 3),
Cis-4-({[(1Z)-2-butyl-2-tert-butyl-1-oxido-1λ$^5$-diazan-1-ylidene]amino}oxy)-cyclohexanecarboxylic acid (Ex 4),
Cis-4-({[(1Z)-2-methyl-1-oxido-(2-propan-2-yl)-1λ$^5$-diazan-1-ylidene]amino}oxy)-cyclohexanecarboxylic acid (Ex 5),
Trans-4-({[(1Z)-2-tert-butyl-2-methyl-1-oxido-1λ$^5$-diazan-1-ylidene]amino}oxy)-cyclohexanecarboxylic acid (Ex 6),
Trans-4-({[(1Z)-2-tert-butyl-2-(2-hydroxyethyl)-1-oxido-1λ$^5$-diazan-1-ylidene]amino}oxy)-cyclohexanecarboxylic acid (Ex 7),
Trans-4-({[(1Z)-2-butyl-2-tert-butyl-1-oxido-1λ$^5$-diazan-1-ylidene]amino}oxy)-cyclohexanecarboxylic acid (Ex 8),
Trans-4-({[(1Z)-2-methyl-1-oxido-(2-propan-2-yl)-1λ$^5$-diazan-1-ylidene]amino}oxy)-cyclohexanecarboxylic acid (Ex 9),
Trans-4-({[(1Z)-2,2-diethyl-1-oxido-1λ$^5$-diazan-1-ylidene]amino}oxy)-cyclohexanecarboxylic acid (Ex 10),
Cis-4-({[(1Z)-2-tert-butyl-2-methyl-1-oxido-1λ$^5$-diazan-1-ylidene]amino}oxy)(1-$^2$H)cyclohexanecarboxylic acid (Ex 11),
Trans-4-({[(1Z)-2-tert-butyl-2-methyl-1-oxido-1λ$^5$-diazan-1-ylidene]amino}oxy)(1-$^2$H)cyclohexanecarboxylic acid (Ex 12),
(1RS,2RS,4RS)-4-({[(1Z)-2-tert-butyl-2-methyl-1-oxido-1λ$^5$-diazan-1-ylidene]amino}oxy)-2-methylcyclohexanecarboxylic acid (Ex 13),
(1RS,2SR,4RS)-4-({[(1Z)-2-tert-butyl-2-methyl-1-oxido-1λ$^5$-diazan-1-ylidene]amino}oxy)-2-methylcyclohexanecarboxylic acid (Ex 14), (1RS,2RS,4RS)-4-({[(1Z)-2-tert-butyl-2-methyl-1-oxido-1λ$^5$-diazan-1-ylidene]amino}oxy)-2-methylcyclohexanecarboxylic acid (Ex 15),
(1RS,2RS,4RS)-4-({[(1Z)-2-tert-butyl-2-methyl-1-oxido-1λ$^5$-diazan-1-ylidene]amino}oxy)-2-methylcyclohexanecarboxylic acid (Ex 16),
(1RS,3RS)-3-({[(1Z)-2-tert-butyl-2-methyl-1-oxido-1λ$^5$-diazan-1-ylidene]amino}oxy)cyclohexanecarboxylic acid (Ex 17),
[4-({[(1Z)-2-tert-butyl-2-methyl-1-oxido-1λ$^5$-diazan-1-ylidene]amino}oxy)cyclohexyl]acetic acid (Ex 18),
3-[4-({[(1Z)-2-tert-butyl-2-methyl-1-oxido-1λ$^5$-diazan-1-ylidene]amino}oxy)cyclohexyl]propanoic acid (Ex 19),
2-({[cis-4-({[(1Z)-2-tert-butyl-2-methyl-1-oxido-1λ$^5$-diazan-1-ylidene]amino}oxy)cyclohexyl]carbonyl}oxy)-N,N,N-trimethylethanaminium trifluoroacetate (Ex 20), or
2-({[cis-4-({[(1Z)-2-tert-butyl-2-ethyl-1-oxido-1λ$^5$-diazan-1-ylidene]amino}oxy)cyclohexyl]carbonyl}oxy)-N,N,N-trimethylethanaminium trifluoro acetate (Ex 21).

Compounds of the invention can be used to treat hypertension, treat angina, improve insulin sensitivity, and provide renal protection. The compounds can be used alone or in a fixed dose combination with other antihypertensives such as, for example, angiotensin II receptor blockers, diuretics, ACE inhibitors, β-blockers, and calcium channel blockers.

Pharmaceutically acceptable salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

Some of the compounds described herein may exist as tautomers. The individual tautomers as well as mixtures thereof are encompassed with the described compounds.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

" 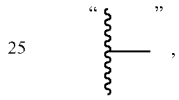 ,"

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

Alkyl groups may be unsubstituted, or substituted with 1 to 3 substituents on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)$S(O)_{0-2}$—, $HS(O)_{0-2}$—, ($C_1$-$C_6$ alkyl)$S(O)_{0-2}$($C_1$-$C_6$ alkyl)-, $HS(O)_{0-2}$($C_1$-$C_6$ alkyl)-, ($C_0$-$C_6$ alkyl)C(O)NH—, $H_2$N—C(NH)—, —$O(C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)$C(O)_{1-2}$($C_1$-$C_6$ alkyl)-, $HC(O)_{1-2}$($C_1$-$C_6$ alkyl)-, ($C_1$-$C_6$ alkyl)$C(O)_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyanoaryl, cyano-aralkyl, cyano-heterocycle and cyano-heterocyclylalkyl, where such substitution results in formation of a stable compound.

The term "aryl", alone or in combination, relates to a phenyl, naphthyl or indanyl group, preferably a phenyl group. The abbreviation "Ph" represents phenyl.

The term "heteroaryl" refers to an unsaturated ring having a specified number of atom members (e.g., 5 or 6-membered), including a specified number of heteroatoms (e.g., 1, 2, 3or 4 heteroatoms independently selected from N, O or S), e.g., 5-membered rings containing one nitrogen (pyrrole), one oxygen (pyran) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (furan) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The term "heterocyclic" refers to a saturated ring having a specified number of atom members and a specified number of heteroatoms, in which the entire ring system (whether mono- or poly-cyclic) is saturated, e.g., a 4- to 8-membered saturated monocyclic ring or a stable 7- to 12-membered bicyclic ring system which consists of carbon atoms and one or more heteroatoms selected from N, O and S, a 5- or 6-membered heterocyclic ring having 1 or 2 heteroatoms which are N, O or S, etc. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Aryl groups may be unsubstituted, or substituted with 1 substituent on any one or more carbon atoms, with halogen, $C_1$-$C_{20}$ alkyl, $CF_3$, $NH_2$, —NH($C_1$-$C_6$ alkyl), —N($C_1$-$C_6$alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$ ($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$ ($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Heteroaryl and heterocyclic rings may be unsubstituted, or substituted with 1 substituent on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl) S(O)$_{0-2}$($C_1$-$C_6$alkyl)-, HS(O)$_{0-2}$($C_1$-$C_6$ alkyl)-, ($C_1$-$C_6$ alkyl) S(O)$_{0-2}$—, ($C_1$-$C_6$ alkyl)C(O)NH—, HC(O)NH—, $H_2$N—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O ($C_1$-$C_6$ alkyl)-, HO($C_1$-$C_6$ alkyl)-, ($C_1$-$C_6$ alkyl)O—, ($C_1$-$C_6$alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$alkynyl, aryl, —C(O)$C_{1-6}$alkyl, —C(O)NH$C_1$-$C_6$ alkyl, —C(O) $NH_2$, —$C_1$-$C_6$ alkylC(O)$NH_2$, —$C_1$-$C_6$ alkylOC(O)$NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

The compounds of the invention are useful for treating hypertension, Pulmonary Arterial Hypertension, congestive heart failure, angina, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of compounds of the invention for the preparation of a medicament for the treatment and/or prophylaxis of the above-mentioned diseases.

The above-mentioned compounds of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S, 5S,7S)—N-(2-carbamoyl-2-methylpropyl)-5-amino-4-hydroxy-2,7-diisopropyl-8-[4-methoxy-3-(3-methoxypropoxy) phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds including (i) PPAR.gamma, agonists, such as the glitazones (e.g. troglitazone, pioglitazone, englitazone, MCC-555, rosiglitazone, balaglitazone, and the like) and other PPAR ligands, including PPAR.alpha./.gamma, dual agonists, such as KRP-297, muraglitazar, naveglitazar, Galida, tesaglitazar, TAK-559, PPAR.alpha. agonists, such as fenofibric acid derivatives (gemfibrozil, clofibrate, fenofibrate and bezafibrate), and selective PPAR.gamma. modulators (SPPAR.gamma.M's), such as disclosed in WO 02/060388, WO 02/08188, WO 2004/019869, WO 2004/

020409, WO 2004/020408, and WO 2004/066963; (ii) biguanides such as metformin and phenformin, and (iii) protein tyrosine phosphatase-1B (PTP-1B) inhibitors, glipizide, DPP-IV inhibitors such as sitagliptin, vildagliptin, alogliptin, and saxagliptin, which inhibit dipeptidyl peptidase-IV enzyme and which are useful for treating diabetes, or with other drugs beneficial for the prevention or the treatment of the above-mentioned diseases including nitroprusside and diazoxide. Such combination can be achieved by combining two active ingredients in a single dosage formulation containing two independent active ingredients, e.g., an angiotensin II receptor antagonist and a nitrooxy cyclopentane derivative of the invention.

The dosage regimen utilizing the compound of the invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds of the invention, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, more preferably 25 mg/day to 150 mg/day, and more preferably 5 mg/day to 100 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the compound of the invention may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The compounds of the invention can be administered in such oral forms as tablets, capsules and granules. The compounds of the invention are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods Of Synthesis

Several methods for preparing the compounds of this invention are described in the following Schemes and Examples. Starting materials and intermediates are made from known procedures or as otherwise illustrated. Variables are as described above unless otherwise indicated.

Scheme 1 describes a convenient method to prepare the sodium diazeniumdiolates of the general structure 1-2 in this invention. The secondary amine 1-1 is treated with nitric oxide at an appropriate temperature such as room temperature in the presence of a suitable base such as sodium hydroxide, sodium methoxide, or sodium tert-butoxide in an appropriate solvent such as acetonitrile, methanol, tetrahydrofuran, N,N-dimethylformamide, or water. Examples on the preparation of the sodium diazeniumdiolates can be found from the literature (Chakrapani, H.; Showalter, B. M.; Citro, M. L.; Keefer, L. K.; Saavedra, J. E. *Org. Lett.* 2007, 9, 4551-4554 and WO Patent 2009/094242.

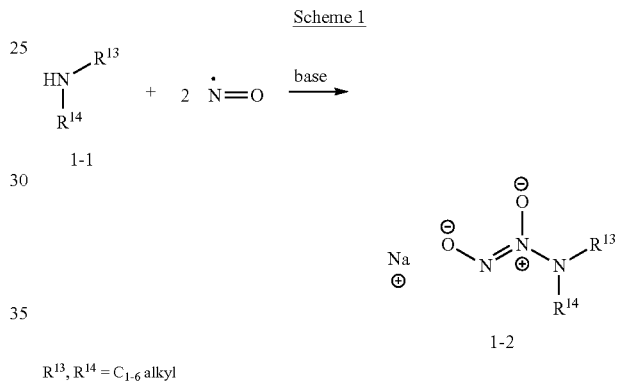

Scheme 2 delineates a method to prepare $O^2$-alkylated diazeniumdiolates of the general structure 2-3 in this invention. Cyclopentanols of the general structure 2-1 can be prepared from reduction of the corresponding ketone, hydroboration/oxidation of the corresponding olefin, and ring opening of the corresponding epoxide. The alcohol 2-1 can be activated for displacement at an appropriate temperature such as room temperature with a suitable reagent such as methanesulfonic anhydride, benzenesulfonyl chloride, 4-(trifluoromethyl) phenylsulfonyl chloride in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. The resultant sulfonate 2-2 can be displaced by the appropriate sodium diazeniumdiolate salt 1-2 at an appropriate temperature such as room temperature in an appropriate solvent such as dichloromethane, dichloroethane, chloroform, acetonitrile, tetrahydrofuran, dioxane, toluene, N,N-dimethylformamide, or N-methylpyrrolidinone. The stereochemistry at the sulfonate carbon is typically inverted as a result of the displacement. Finally, deprotection of 2-3 gave 2-4.

Scheme 2

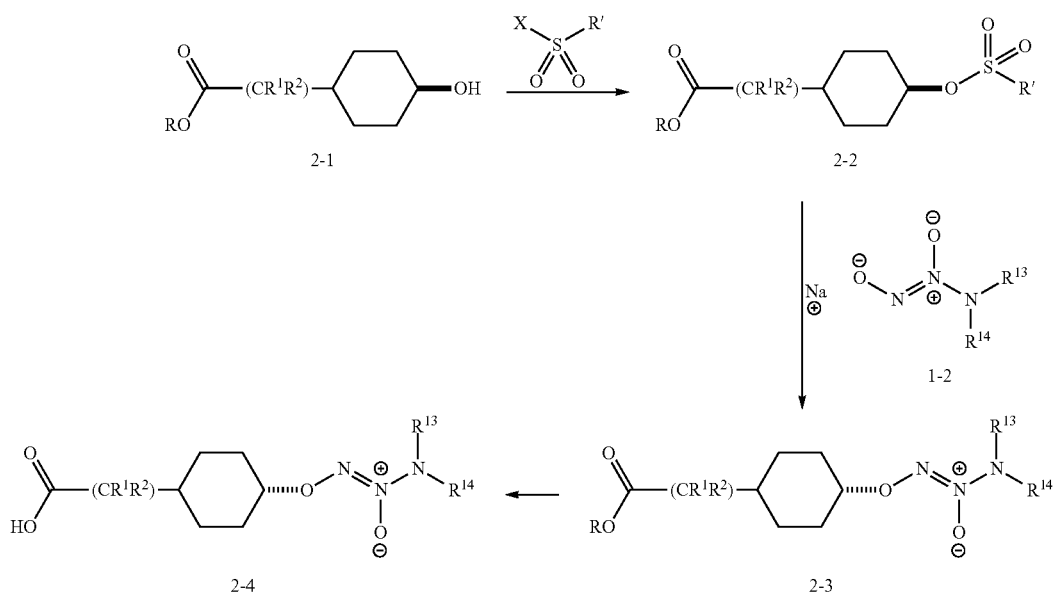

X = Cl, OSO$_2$R$^{15}$
R = C$_{1-6}$ alkyl, benzyl
R' = methyl, CF$_3$, 4-methylphenyl, 4-trifluoromethylphenyl
R$^{13}$, R$^{14}$ = ——C$_{1-6}$alkyl, ——(CH$_2$)$_{2-6}$OH, ——(CH$_2$)$_{2-6}$OC$_{1-6}$alkyl General Procedures Reactions sensitive to moisture or air were performed under nitrogen or argon using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass®ZQ™ with electrospray ionization in positive ion detection mode. High performance liquid chromatography (HPLC) was conducted on an Agilent 1100 series HPLC on Waters C18 XTerra 3.5 µm 2.1×20 mm column with gradient 10:90-98:2 v/v CH$_3$CN/H$_2$O+v 0.05% TFA over 1.25 min then hold at 98:2 v/v CH$_3$CN/H$_2$O+v 0.05% TFA for 0.75 min; flow rate 1.5 mL/min, UV wavelength 254 nm (noted as LC-1) or on Waters C$_{18}$ XTerra 3.5 µm 3×50 mm column with gradient 10:90-98:2v/v CH$_3$CN/H$_2$O+v 0.05% TFA over 3.75 min then hold at 98:2 v/v CH$_3$CN/H$_2$O+ v 0.05% TFA for 1.75 min; flow rate 1.0 mL/min, UV wavelength 254 nm (noted as LC-2). Concentration of solutions was carried out on a rotary evaporator under reduced pressure. Flash chromatography was performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak AS, Chiralpak AD, Chiralcel OD, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, or Chiralcel OJ columns (20×250 mm) (Daicel Chemical Industries, Ltd.) with desired isocratic solvent systems identified on chiral analytical chromatography.

Abbreviations: acetic acid (AcOH), aqueous (aq), (benzotriazol-1-yloxy)tripyrrolidino-phosphonium hexafluorophosphate (PyBOP), ethyl acetate (EtOAc), diethyl ether (ether or Et$_2$O), dichloromethane (DCM), N,N-diisopropylethylamine (DIEA), 4-(N,N-dimethylamino) pyridine (DMAP), N,N-dimethylfonnamide (DMF), gram(s) (g), 2-(7-Aza-1H-benzotriazole-1-yl)-1,1,3,3-tetramethyluronium hexafluorophosphate (HATU), hour(s) (h or hr), microliter(s) (µL), milHgram(s) (mg), milliliter(s) (mL), millimole (mmol), mass spectrum (ms or MS), 2-propanol (IPA), retention time (R$_t$), room temperature (rt), saturated aq sodium chloride solution (brine), triethylamine (Et$_3$N), trifluoroacetic acid (TFA), tetrahydrofuran (THF), and minute(s) (min).

Example 1

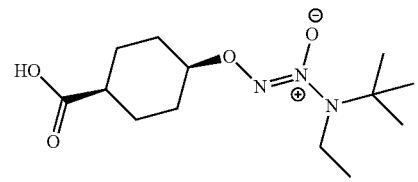 [SMILES: CCN(/[N+]([O-])=N/O[C@H]1CC[C@@H](C(=O)O)CC1)C(C)(C)C]

Cis-4-({[(1Z)-2-tert-butyl-2-ethyl-1-oxido-1λ⁵-diazan-1-ylidene]amino}oxy)-cyclohexanecarboxylic acid

Step A: Ethyl Trans-4-hydroxycyclohexanecarboxylate

To a solution of raw-4-hydroxycyclohexanecarboxylic acid (25 g, 173 mmol) in 200 ml ethanol was added concentrated sulfuric acid (8.50 g, 87.0 mmol). After heating at 100° C. over night, the mixture was concentrated down and then partitioned between DCM (300 ml) and water (300 ml). The organic layer was washed with brine, dried over $MgSO_4$, filtered and concentrated down to give the title compound: $^1H$ NMR (500 MHz, $CDCl_3$) δ 4.14 (m, 2H), 3.63 (m, 1H), 2.25 (m, 1H), 2.04 (m, 4H), 1.70 (bs, 1H), 1.50 (m, 2H), 1.34-1.25 (m, 5H).

Step B: ethyl trans-4-({[4-trifluoromethyl)phenyl]sulfonyl}oxy)cyclohexanecarboxylate To a solution of ethyl trans-4-hydroxycyclohexanecarboxylate (26.0 g, 151.0 mmol) in 500 ml $CH_2Cl_2$ at 0° C. was added $Et_3N$ (22.91 g, 226.0 mmol) and DMAP (1.84 g, 15.10 mmol), and followed by 4-(trifluoromethyl)benzenesulfonyl chloride (40.6 g, 166.6 mmol). After stirring at 0° C. for 1 hr and then at rt for 1 hr, the mixture was concentrated and the residue was partitioned between ether (300 ml) and water (300 ml). The organic layer was washed with brine, dried over $MgSO_4$, and concentrated. The residue was purified by flash chromatography (Biotage 2×65+M) using 0 to 30% EtOAc/hexane gradient, affording the title compound: $^1H$ NMR (500 MHz, $CDCl_3$) δ 8.07 (d, J=8.4 Hz, 2H), 7.85 (d, J=8.4 Hz, 2H), 4.56 (m, 1H), 4.12 (m, 2H), 2.29 (m, 1H), 2.02 (m, 4H), 1.55 (m, 4H), 1.24 (t, 3H).

Step C: ethyl cis-4-({[(1Z)-2-tert-butyl-2-ethyl-1-oxido-1λ⁵-diazan-1-ylidene]amino}oxy)cyclohexanecarboxylate To a solution of ethyl trans-4-({[4-(trifluoromethyl) phenyl]sulfonyl}oxy)cyclohexanecarboxylate (20.0 g, 52.6 mmol) in 150 ml DMF was added sodium (1Z)-3-tert-butyl-3-ethyltriaz-1-en-1-olate 2-oxide (11.56, g, 63.1 mmol). After stirring at 45° C. for 16 hr, the mixture was partitioned between ether (300 ml) and water (300 ml). The organic layer was washed with brine, dried over $MgSO_4$, and concentrated. The residue was purified by flash chromatography (Biotage 65+M) using 0 to 30% EtOAc/hexane gradient, affording the title compound: $^1H$ NMR (500 MHz, $CDCl_3$) δ 4.46 (m, 1H), 4.14 (m, 2H), 3.10 (m, 2H), 2.40 (m, 1H), 2.00 (m, 4H), 1.75 (m, 4H), 1.27 (s, 9H), 1.04 (t, 3H).

Step D: cis-4-({[(1Z)-2-tert-butyl-2-ethyl-1-oxido-1λ⁵-diazan-1-ylidene]amino}oxy)cyclohexanecarboxylic acid To a solution of ethyl cis-4-({[(1Z)-2-tert-butyl-2-ethyl-1-oxido-1λ⁵-diazan-1-ylidene]amino}oxy)cyclohexanecarboxylic (2.0 g, 6.34 mmol) in 15 ml ethanol at rt was added 5N NaOH (4.0 ml, 20.0 mmol). After stirring at rt for 3 hr, the mixture was concentrated. The residue was partitioned between ether (30 ml) and 1N HCl (20 ml). The organic layer was washed with brine, dried over $MgSCO_4$, and concentrated to give the title compound: $^1H$ NMR (500 MHz, $CDCl_3$) δ 4.48 (m, 1H), 3.11 (m, 3H), 2.48 (m, 1H), 2.00 (m, 4H), 1.77 (m, 4H), 1.25 (s, 9H), 1.04 (t, 3H).

Example 2

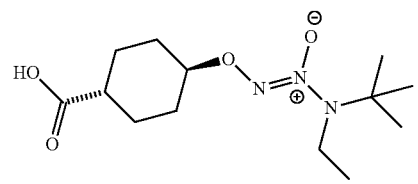 [SMILES: CCN(/[N+]([O-])=N/O[C@H]1CC[C@H](C(=O)O)CC1)C(C)(C)C]

Trans A-({[(1Z)-2-tert-butyl-2-ethyl-1-oxido-1λ⁵-diazan-1-ylidene]amino}oxy)-cyclohexanecarboxylic acid This example was prepared using procedures described for EXAMPLE 1 substituting trans-hydroxycyclohexanecarboxylic acid with cis-4-hydroxycyclohexanecarboxylic acid in Step A.

Examples 3-5

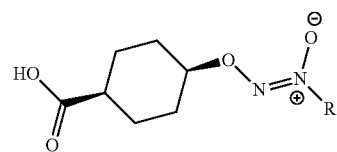

The following examples were prepared using procedures analogous to those described for example 1 substituting appropriate sodium salt for sodium (1Z)-3-tert-butyl-3-ethyltriaz-1-en-1-olate 2-oxide in Step C.

| Example | R | HPLC $R_t$ (min) | MS (M + H/M + Na) |
|---|---|---|---|
| 3 | ![N-tBu] | 2.42 (LC-2) | 274/296 |
| 4 | ![N(butyl)-tBu] | 3.31 (LC-2) | 316/338 |
| 5 | ![N(Me)-iPr] | 0.95 (LC-1) | 260/282 |

Examples 6-10

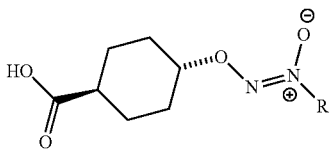

The following examples were prepared using procedures analogous to those described for example 2 substituting appropriate sodium salt for sodium (1Z)-3-tert-butyl-3-ethyltriaz-1-en-1-olate 2-oxide in Step C.

| Example | R | HPLC R_t (min) | MS (M + H/M + Na) |
|---------|---|----------------|-------------------|
| 6 | (tert-butyl-N-methyl) | 2.45 (LC-2) | 274/296 |
| 7 | (tert-butyl-N-CH2CH2OH) | 0.32 (LC-1) | 332/354 |
| 8 | (tert-butyl-N-butyl) | 3.27 (LC-2) | 316/338 |
| 9 | (isopropyl-N-methyl) | 0.95 (LC-1) | 260/282 |
| 10 | (N,N-diethyl-ethyl) | 2.35 (LC-2) | 260/282 |

Example 11

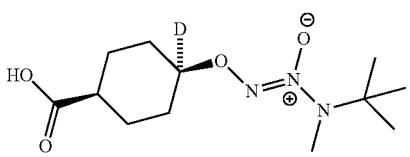 [SMILES: [2H][C@]1(O/N=[N+](\[O-])N(C)C(C)(C)C)CC[C@@H](C(=O)O)CC1]

Cis-4-({[(1Z)-2-tert-butyl-2-methyl-1-oxido-1λ⁵-diazan-1-ylidene]amino}oxy)(1-²H)cyclohexanecarboxylic acid

Step A: ethyl 4-hydroxy(4-²H)cyclohexanecarboxylate

To a solution of ethyl 4-oxocyclohexanecarboxylate (4.0 g, 23.5 mmol) in 40 mL EtOH at 0° C. was added sodium borodeuteride (1.180 g, 28.2 mmol). After stirring at 0° C. for 3 hrs, the mixture was concentrated and then partitioned between EtOAc (150 ml) and water (150 ml). The aqueous layer was separated, extracted with ether (2×150 mL). The organic layers were combined, dried over MgSO₄, filtered and concentrated. The residue as purified by Biotage 50 g snap on column with 0-50% EtOAc in hexane, to give the title compound.

Step B: ethyl 4-({[4-(trifluoromethyl)phenyl]sulfonyl}oxy)(1-²H)cyclohexanecarboxylate To a solution of ethyl 4-hydroxy(4-²H)cyclohexanecarboxylate (4.0 g, 23.09 mmol) in 100 ml CH₂Cl₂ at 0° C. was added Et₃N (4.67 g, 46.2 mmol) and DMAP (0.28 g, 2.31 mmol), followed by 4-(trifluoromethyl)benzenesulfonyl chloride (8.47 g, 34.6 mmol). After stirring at 0° C. for 1 hr and then at rt for 1 hr, the mixture was concentrated and the residue was partitioned between ether (300 ml) and water (300 ml). The organic layer was washed with brine, dried over MgSO₄, and concentrated. The residue was purified by flash chromatography (Biotage 40+M) using 0 to 30% EtOAc/hexane gradient, affording the title compound.

Step C: ethyl 4-({[(1Z)-2-tert-butyl-2-methyl-1-oxido-1λ⁵-diazan-1-ylidene]amino}oxy)(1-²H)cyclohexanecarboxylate To a solution of ethyl 4-({[4-(trifluoromethyl)phenyl]sulfonyl}oxy)(1-²H)cyclohexanecarboxylate (8.26 g, 21.66 mmol) in 50 ml DMF was added sodium (1Z)-3-tert-butyl-3-methyltriaz-1-en-1-olate 2-oxide (6 g, 35.5 mmol). After stirring at 45° C. for 16 hr, the mixture was partitioned between ether (300 ml) and water (300 ml). The organic layer was washed with brine, dried over MgSO₄, and concentrated. The residue was purified by flash chromatography (Biotage 65+M) using 0 to 30% EtOAc/hexane gradient, affording the title compound.

Step D: cis-4-({[(1Z)-2-tert-butyl-2-methyl-1-oxido-1λ⁵-diazan-1-ylidene]amino}oxy)(1-²H)cyclohexanecarboxylic acid To the solution of ethyl cis-4-({[(1Z)-2-tert-butyl-2-methyl-1-oxido-1λ⁵-diazan-1-ylidene]amino}oxy) (1-²H)cyclohexanecarboxylate (0.82 g, 2.71 mmol) which was separated by chiral OJ column with 10% MeOH/CO2 fast elution peak in 15 ml ethanol at rt was added 5N NaOH (2.0 ml, 10.0 mmol). After stirring at rt for 3 hr, the mixture was concentrated. The residue was partitioned between ether (30 ml) and 1N HCl (20 ml). The organic layer was washed with brine, dried over MgSO₄, and concentrated to give the title compound: ¹H NMR (500 MHz, CDCl₃) δ 2.80 (s, 3H), 2.46 (m, 1H), 2.00 (m, 4H), 1.76 (m, 4H), 1.23 (s, 9H).

Example 12

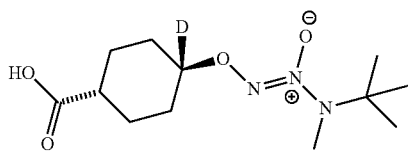 [SMILES: [2H][C@]1(O/N=[N+](\[O-])N(C)C(C)(C)C)CC[C@H](C(=O)O)CC1]

Trans-4-({[(1Z)-2-tert-butyl-2-methyl-1-oxido-1λ⁵-diazan-1-ylidene]amino}oxy)(1-²H)cyclohexanecarboxylic acid To the solution of ethyl trans-4-({[(1Z)-2-tert-butyl-2-methyl-1-oxido-1λ⁵-diazan-1-ylidene]amino}oxy) (1-²H)cyclohexanecarboxylate (0.76 g, 2.51 mmol) which was separated by chiral OJ column with 10% MeOH/CO2 slow elution peak in 15 ml ethanol at rt was added 5N NaOH (2.0 ml, 10.0 mmol). After stirring at rt for 3 hr, the mixture was concentrated. The residue was partitioned between ether (30 ml) and 1N HCl (20 ml). The organic layer was washed with brine, dried over MgSO₄, and concentrated to give the title compound: ¹H NMR (500 MHz, CDCl₃) δ 2.72 (s, 3H), 2.26 (m, 1H), 2.13 (m, 2H), 2.04 (m, 2H), 1.48 (m, 4H), 1.15 (s, 9H).

Examples 13 and 14

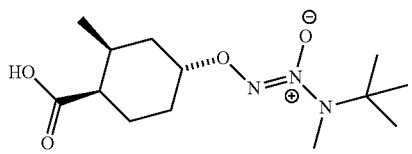 [SMILES: C[C@H]1C[C@H](O/N=[N+](\[O-])N(C)C(C)(C)C)CC[C@H]1C(=O)O]

(1RS,2RS, 4RS)-4-({[(1Z)-2-tert-butyl-2-methyl-1-oxido-1λ⁵-diazan-1-ylidene]amino}oxy)-2-methyl-cyclohexanecarboxylic acid

Step A: ethyl (1RS,2SR)-2-methyl-4-oxocyclohexanecarboxylate

To the solution of ethyl 2-methyl-4-oxocyclohex-2-ene-1-carboxylate (20.0 g, 110 mmole) in 300 ml ethanol was added Pd/C (3.5 g, 3.29 mmol), followed by 3.0M HCl (2.0 ml, 6.0 mmol). It was put on Parr Shaker Apparatus for 2.5 hour at 50 psi room temperature. The catalyst was removed by filtration, after concentrate, the residue was purified by flash chromatography (Biotage 340) using 0 to 20% EtOAc/hexane gradient, affording the title compound.

Step B: ethyl (1RS,2SR)-4-hydroxy-2-methylcyclohexanecarboxylate

To a at solution of ethyl (1RS,2SR)-2-methyl-4-oxocyclohexanecarboxylate (20.0 g, 109 mmol) in 800 ml ethanol 0° C. was added NaBH₄ (4.93 g, 130 mmol), after 1.5 hour, the mixture was concentrated and the residue was partitioned between ether (600 ml) and water (600 ml). The organic layer was washed with brine, dried over MgSO₄, and concentrated. The residue was purified by flash chromatography (Biotage 340) using 30 to 70% EtOAc/hexane gradient, affording the title compound.

Step C: ethyl (1RS,2SR)-4-iodo-2-methylcyclohexanecarboxylate

To the solution of ethyl (1RS,2SR)-4-hydroxy-2-methyl-cyclohexanecarboxylate (22.2 g, 114 mmol) in 300 mL CH₂Cl₂ at 0° C. was added imidazole (7.76 g, 114.0 mmol), then triphenylphosphine (29.9 g, 114.0 mmol) was added. After all the material were dissolved, iodine (28.9 g, 114.0 mmol) was added in several portions over a period of 45 minutes. The resulting suspension was gradually allowed to warm up to rt and stirred over night. The mixture was partitioned between Et₂O 300 mL and water 300 mL. The organic layer was washed with saturated Na2S₂O₃ 150 mL and brine 3×100 mL, dried over MgSO₄, filtered and concentrated down. The residue was purified by flash chromatography (Biotage 340) using 0-20% ethyl acetate/hexane gradient, affording the title compound.

Step D: ethyl (1RS,2SR,4RS)-4-({[(1Z)-2-tert-butyl-2-methyl-1-oxido-1λ⁵-diazan-1-ylidene]amino}oxy)-2-methylcyclohexanecarboxylate To a solution of ethyl (1RS,2SR)-4-iodo-2-methylcyclohexanecarboxylate (19.1 g, 64.4 mmol) in 100 ml DMF was added sodium (1Z)-3-tert-butyl-3-methyltriaz-1-en-1-olate 2-oxide (14.2 g, 84.0 mmol). After stirring at 45° C. for 16 hr, the mixture was partitioned between ether (300 ml) and water (300 ml). The organic layer was washed with brine, dried over MgSO₄, and concentrated. The residue was purified by flash chromatography (Biotage 340) using 0 to 20% EtOAc/hexane gradient, affording the title compound: ¹H NMR (500 MHz, CDCl₃) δ 4.07 (m, 1H), 3.88 (m, 2H), 2.56 (s, 3H), 2.32 (m, 1H), 1.83 (m, 1H), 1.77 (m, 4H), 3.38 (m, 1H), 1.00 (m, 11H), 0.83 (t, 3H).

Step E: (1RS,2SR,4RS)-4-({[(1Z)-2-tert-butyl-2-methyl-1-oxido-1λ⁵-diazan-1-ylidene]amino}oxy)-2-methylcyclohexanecarboxylic acid The enantiomers of ethyl (1RS,2SR,4RS)-4-({[(1Z)-2-tert-butyl-2-methyl-1-oxido-1λ⁵-diazan-1-ylidene]amino }oxy)-2-methylcyclohexanecarboxylate were separated by chiral OJ column with 10% MeOH/CO₂. To a solution of the fast elution peak in 15 ml ethanol at rt was added 5N NaOH (3.0 ml, 15.0 mmol). After stirring at rt for 3 hr, the mixture was concentrated. The residue was partitioned between ether (30 ml) and 1N HCl (20 ml). The organic layer was washed with brine, dried over MgSO₄, and concentrated to give the title compound.

The acid of the other enantiomer was prepared according to the same hydrolysis procedure.

Examples 15 and 16

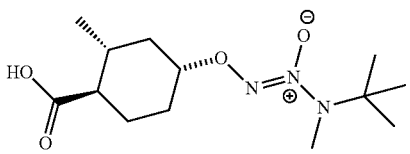 [SMILES: C[C@@H]1C[C@H](O/N=[N+](\[O-])N(C)C(C)(C)C)CC[C@H]1C(=O)O]

(1RS,2SR)-4-({[(1Z)-2-tert-butyl-2-methyl-1-oxido-
1λ⁵-diazan-1-ylidene]amino}oxy)-2-methylcyclo-
hexanecarboxylic acid

Step A: ethyl (7SR,8RS)-7-methyl-1,4-dioxaspiro[4.5]decane-8-carboxylate

To the solution of ethyl (1RS,2SR)-2-methyl-4-oxocyclohexanecarboxylate (21.1 g, 109 mmol) in 200 ml toluene was added toluenesulfonic acid (1.04 g, 5.46 mmol), followed by ethylene glycol (8.13 g, 131 mmol). The mixture was heated at 120° C. with Dean-Stark over night. The mixture was cooled down to room temperature and concentrated. The residue was purified by flash chromatography (Biotage 340) using 0 to 20% EtOAc/hexane gradient, affording the title compound: $^1$H NMR (500 MHz, CDCl$_3$) δ 4.15 (m, 2H), 3.96 (m, 4H), 2.55 (m, 1H), 2.15 (m, 1H), 2.00-1.80 (m, 4H), 1.58 (m, 2H), 1.26 (m, 3H), 1.00 (t, 3H).

Step B: ethyl (7RS,8RS)-7-methyl-1,4-dioxaspiro[4.5]decane-8-carboxylate

To the solution of ethyl (7SR,8RS)-7-methyl-1,4-dioxaspiro[4.5]decane-8-carboxylate (15.2 g, 66.1 mmol) in 250 ml tert-butanol was added potassium tert-butoxide (1.11 g, 9.92 mmol), the mixture was heated at 95° C. over night. The mixture concentrated down, the residue was partitioned between ether (300 ml) and water (300 ml). The organic layer was washed with brine, dried over MgSO$_4$, and concentrated to afford the title compound: $^1$H NMR (500 MHz, CDCl$_3$) δ 3.96 (m, 2H), 3.75 (m, 4H), 1.82-1.55 (m, 6H), 1.30 (m, 1H), 1.07 (m, 4H), 0.72 (t, 3H).

Step C: ethyl (1RS,2RS)-methyl-4-oxocyclohexanecarboxylate

The solution of ethyl (7RS,8RS)-7-methyl-1,4-dioxaspiro[4.5]decane-8-carboxylate (21.1 g, 92 mmol) in 50 ml formic acid and 2 ml water was stirred at room temperature over night. After concentrated down, the residue was partitioned between ether (300 ml) and water (300 ml). The organic layer was washed with brine, dried over MgSO$_4$, and concentrated to afford the title compound: $^1$H NMR (500 MHz, CDCl$_3$) δ 4.20 (m, 2H), 2.50-1.90 (m, 8H), 1.30 (m, 3H), 1.05 (m, 3H).

Step D: ethyl (1RS,2RS, 4RS)-4-({[(1Z)-2-tert-butyl-2-methyl-1-oxido-λ⁵-diazan-1-ylidene]amino}oxy)-2-methylcyclohexanecarboxylate The title compound was prepared using procedures described for EXAMPLE 12 from Step B to D, substituting ethyl (1RS,2RS)-2-methyl-4-oxocyclohexanecarboxylate for ethyl (1RS,2RS)-2-methyl-4-oxocyclohexanecarboxylate: $^1$H NMR (500 MHz, CDCl$_3$) δ 4.19 (m, 1H), 4.03 (m, 2H), 2.70 (s, 3H), 2.10 (m, 2H), 1.88 (m, 2H), 1.70 (m, 1H), 1.40 (m, 2H), 1.08 (m, 13H), 0.84 (t, 3H).

Step E: (1RS,2RS,4RS)-4-({[(1Z)-2-tert-butyl-2-methyl-1-oxido-1λ⁵-diazan-1-ylidene]amino}oxy)-2-methylcyclohexanecarboxylic acid The title compound was prepared using procedures described for EXAMPLE 12 substituting ethyl (1RS,2RS,4RS)-4-({[(1Z)-2-tert-butyl-2-methyl-1-oxido-λ⁵-diazan-1-ylidene]amino}oxy)-2-methylcyclohexanecarboxylate for ethyl (1RS,2RS,4RS)-4-({[(1Z)-2-tert-butyl-2-methyl-1-oxido-1λ⁵-diazan-1-ylidene]amino}oxy)-2-methylcyclohexanecarboxylate in Step E. LC/MS (LC-2): t$_R$=2.81 min, M+H=288.20.

Example 17

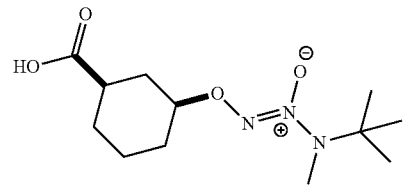 [SMILES: CN(/[N+]([O-])=N/O[C@H]1CCC[C@@H](C(=O)O)C1)C(C)(C)C]

(1RS,3SR)-3-({[(1Z)-2-tert-butyl-2-methyl-1-oxido-
1λ⁵-diazan-1-ylidene]amino}oxy)cyclohexanecarboxylic acid

Step A: 3-hydroxycyclohexanecarboxylic acid

A solution of 3-hydroxybenzoic acid (20.0 g, 145 mmol) in 600 mL EtOAc containing acetic acid (10.49 g, 175 mmol) and rhodium (3.0 g, 1.46 mmol) was put on hydrogenation apparatus at 100 psi and 80° C. for 18 hours. After the catalyst was removed by filtration, the filtrate was concentrated down to afford the title compound.

Step B: benzyl (1SR,3RS)-3-hydroxycyclohexanecarboxylate

To a solution of 3-hydroxycyclohexanecarboxylic acid (19.5 g, 149 mmol) in 180 mL DMF at room temperature was added benzyl chloride (18.83 g, 149 mmol), followed by Et$_3$N (42.1 g, 406 mmol). The mixture was stirred at room temperature over night. The precipitate was removed by filtration, and the filtrate was diluted ether (300 ml) and washed with water (2×300 ml) and brine, dried over MgSO$_4$, and concentrated. The residue was purified by flash chromatography (Biotage 65M) using 0 to 50% EtOAc/hexane gradient, affording the title compound: $^1$H NMR (500 MHz, CDCl$_3$) δ 7.35 (m, 5H), 5.13 (s, 2H), 4.09 (m, 1H), 2.85 (m, 1H), 12.40 (m, 1H), 2.00-1.60 (m, 8H).

Step C: benzyl (1SR,3SR)-3-iodocyclohexanecarboxylate

To a solution of benzyl (1SR,3RS)-3-hydroxycyclohexanecarboxylate (7.88 g, 33.6 mmol) in CH$_2$Cl$_2$ (150 mL) at 0° C. was added imidazole (6.87 g, 101 mmol), triphenylphosphine (13.23 g, 50.5 mmol), and followed by iodine (14.51 g, 57.2 mmol) in several portions over a period of 45 min. The resulting suspension was gradually allowed to warm up to rt. After stirring at rt over night, the mixture was partitioned between Et$_2$O (200 mL) and water (200 mL). The organic layer was washed with saturated Na$_2$S$_2$O$_3$ (100 mL) and brine (3×100 mL), dried over MgSO$_4$, and concentrated. The residue was purified by flash chromatography (Biotage 40+M) using 10-20% EtOAc/hexane gradient, affording the title compound: $^1$H NMR (500 MHz, CDCl$_3$) δ 7.38 (m, 5H), 5.15 (s, 2H), 4.83 (m, 1H), 2.90 (m, 1H), 2.30 (m, 1H), 2.00 (m, 3H), 1.80 (m, 1H), 1.65 (m, 3H).

Step D: benzyl (1RS,3RS)-3-({[(1Z)-2-tert-butyl-2-methyl-1-oxido-1λ$^5$-diazan-1-ylidene]amino}oxy)cyclohexanecarboxylate To a solution of benzyl (1SR,3SR)-3-iodocyclohexanecarboxylate (9.14 g, 34.5 mmol) in 150 mL DMF was added sodium (1Z)-3-tert-butyl-3-methyltriaz-1-en-1-olate 2-oxide (5.84 g, 34.5 mmol). After stirring at 45° C. for 16 hr, the mixture was partitioned between ether (300 mL) and water (300 mL). The organic layer was washed with brine, dried over MgSO$_4$, and concentrated. The residue was purified by flash chromatography (Biotage 40M) using 0 to 20% EtOAc/hexane gradient, affording the title compound: $^1$H NMR (500 MHz, CDCl$_3$) δ 7.34 (m, 5H), 5.12 (s, 2H), 4.23 (m, 1H), 2.80 (s, 3H), 2.58 (m, 1H), 2.43 (m, 1H), 2.15 (m, 1H), 1.90 (m, 1H), 1.66 (, m, 1H), 1.45 (m, 2H), 1.35 (m, 2H), 1.22 (s, 9H).

Step E: (1RS,3SR)-3-({[(1Z)-2-tert-butyl-2-methyl-1-oxido-1λ$^5$-diazan-1-ylidene]amino}oxy)cyclohexanecarboxylic acid To a solution of benzyl (1RS,3SR)-3-({[(1Z)-2-tert-butyl-2-methyl-1-oxido-1λ$^5$-diazan-1-ylidene]amino}oxy)cyclohexanecarboxylate (1.0 g, 2.75 mmol) in 15 mL ethanol at rt was added 5N NaOH (2.21 mL, 11.01 mmol). After stirring at rt for 3 hr, the mixture was concentrated. The residue was partitioned between ether (30 ml) and 1N HCl (20 ml). The organic layer was washed with brine, dried over MgSO$_4$, and concentrated to give the title compound: $^1$H NMR (500 MHz, CDCl$_3$) δ 4.28 (m, 1H), 2.84 (s, 3H), 2.60 (m, 1H), 2.48 (m, 2H), 2.10 (m, 1H), 2.00 (m, 2H), 1.70 (m, 1H), 1.50 (m, 1H), 1.40 (m, 1H), 1.26 (s, 9H).

Example 18

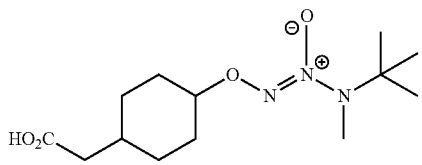 [SMILES: CN(/[N+]([O-])=N/OC1CCC(CC(=O)O)CC1)C(C)(C)C]

[4-({[(1Z)-2-tert-butyl-2-methyl-1-oxido-1λ$^5$-diazan-1-ylidene]amino}oxy)cyclohexyl]acetic acid Step A: ethyl 1,4-dioxaspiro[4.5]dec-8-ylideneacetate Triethylphosphonoacetate (63.3 mmol, 14.19 g) was added to a suspension of NaH (60%) (2.53 g) in THF (100 ml) at 0° C. and the mixture was stirred for 30 min at the same temperature. Then, to the mixture was dropped 1,4-cyclohexanedione monoethylene acetal (57.5 mmol, 8.98 g) in THF (30 ml) at 0° C. and stirring was continued for 1 h. After addition of water, the mixture was extracted with Et$_2$O. The aqueous layer was extracted with EtOAc and combined organic solution was washed with brine, dried over NaSO$_4$, and concentrated under reduced pressure to provide the title compound.

Step B: ethyl 1,4-dioxaspiro[4.5]dec-8-ylacetate

To the solution of ethyl 1,4-dioxaspiro[4.5]dec-8-ylideneacetate (13 g, 57.5 mmol) in EtOAc (100 ml) was added 10% (w/w) Pd/C (2 g) and the mixture was stirred under atmospheric pressure of H$_2$ for 3 h at room temperature. Then, the reaction mixture was filtered through a Celite pad eluting with EtOAc, and concentrated under reduced pressure to afford the title compound.

Step C: ethyl (4-oxocyclohexyl)acetate

To a solution of ethyl 1,4-dioxaspiro[4.5]dec-8-ylacetate (13.01 g, 57.0 mmol) in formic acid (90 ml) was added water (1.54 g, 86.0 mmol). After stirring at rt overnight, formic acid was removed by reduced pressure. The mixture was partitioned between CH$_2$Cl$_2$ (300 ml) and water (300 ml). The organic layer was washed with brine, dried over NaSO$_4$, and concentrated to provide the title compound.

Step D: ethyl (4-hydroxycyclohexyl)acetate

To a solution of ethyl (4-oxocyclohexyl)acetate (10.5 g, 57.0 mmol) in methanol (100 ml) at 0° C. was added NaBH$_4$ (3.23 g, 86.0 mmol) in several portions. The mixture was stirred at 0° C. for 2 h and then it was concentrated. The residue was partitioned between ether (300 ml) and water (300 ml). The organic layer was separated, washed with brine, dried over NaSO$_4$, and concentrated. The residue was purified by flash chromatography using 0 to 50% EtOAc/hexane gradient, affording the title compound.

Step E: ethyl [4-({[4-(trifluoromethyl)phenyl]sulfonyl}oxy)cyclohexyl]acetate

To a solution of ethyl (4-hydroxycyclohexyl)acetate (8.0 g, 43.0 mmol) in 100 ml CH$_2$Cl$_2$ at 0° C. was added Et$_3$N (6.52 g, 64.4 mmol) and DMAP (0.525 g, 4.30 mmol), followed by 4-(trifluoromethyl)benzenesulfonyl chloride (11.56 g, 47.2 mmol). After warming to rt and stirring overnight, the mixture was concentrated and the residue was partitioned between CH$_2$Cl$_2$ (200 ml) and water (200 ml). The organic layer was washed with brine, dried over NaSO$_4$, and concentrated. The residue was purified by flash chromatography on silica gel using 10 to 40% EtOAc/hexane gradient, affording the title compound.

Step F: ethyl [4-({[(1Z)-2-tert-butyl-2-methyl-1-oxido-1λ$^5$-diazan-1-ylidene]amino}oxy)cyclohexyl]acetate To a solution of ethyl [4-({[4-(trifluoromethyl)phenyl]sulfonyl}oxy)cyclohexyl]acetate (3.94 g, 10.0 mmol) in 20 ml DMF was added sodium 1-(N-tert-butylmethylamino)diazen-1-ium-1,2-diolate (1.86 g, 11.0 mmol). After stirring at 45° C. for overnight, the mixture was partitioned between ether (300 ml) and water (300 ml). The organic layer was washed with brine, dried over NaSO$_4$, and concentrated. The residue was purified by flash chromatography on silica gel using 10% to 40% EtOAc/hexane gradient, affording the title compound.

Step G: [4-({[(1Z)-2-tert-butyl-2-methyl-1-oxido-1λ⁵-diazan-1-ylidene]amino}oxy)cyclohexyl]acetic acid To the solution of ethyl [4-({[(1Z)-2-tert-butyl-2-methyl-1-oxido-1λ⁵-diazan-1-ylidene]amino}oxy)cyclohexyl]acetate (795 mg, 2.52 mmol) in Ethanol was added NaOH aqueous solution (252 mg, 6.30 mmol). After stirring at rt overnight and concentration, the mixture was partitioned between ether (100 ml) and water (100 ml). The organic layer was washed with brine, dried over NaSO₄, and concentrated. The residue was purified by flash chromatography on silica gel using 30% to 100% EtOAc/hexane gradient, affording the title compound: ¹H NMR (500 MHz, CDCl₃) δ 4.48 (m, 1H), 2.79 (s, 3H), 2.27 (d, 1.5H), 2.23 (d, 0.5H), 2.05-2.23 (m, 1H), 1.90 (m, 2H), 1.60 (m, 4H), 1.41 (m, 2H), 1.21 (s, 9H).

Example 19

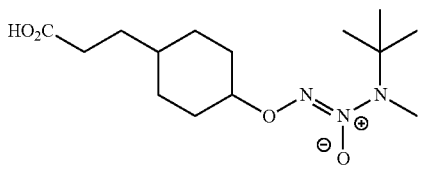 [SMILES: CN(/[N+]([O-])=N/OC1CCC(CCC(=O)O)CC1)C(C)(C)C]

3-[4-({[(1Z)-2-tert-butyl-2-methyl-1-oxido-1λ⁵-diazan-1-ylidene]amino}oxy)cyclohexyl]propanoic acid

Step A: ethyl 3-[4-({[4-(trifluoromethyl)phenyl]sulfonyl}oxy)cyclohexyl]propanoate To a solution of ethyl 3-(4-oxocyclohexyl)propanoate (2.0 g, 10.1 mmol) in methanol (100 ml) at 0° C. was added NaBH₄ (0.57 g, 15.1 mmol) in several portions. The mixture was stirred at 0° C. for 2 hr and then it was concentrated. The residue was partitioned between the diethyl ether (100 ml) and water (100 ml). The organic layer was separated, washed with brine, dried over NaSO₄, and concentrated. The residue was purified by flash chromatography using 40 to 70% EtOAc/hexane gradient, affording the title compound.

Step B: ethyl 3-[4-({[4-(trifluoromethyl)phenyl]sulfonyl}oxy)cyclohexyl]propanoate To a solution of ethyl 3-[4-({[4-(trifluoromethyl)phenyl]sulfonyl}oxy)cyclohexyl]propanoate (2.0 g, 9.99 mmol) in 100 ml CH₂Cl₂ at 0° C. was added Et₃N (1.52 g, 15.0 mmol) and DMAP (0.122 g, 1.0 mmol), followed by 4-(trifluoromethyl)benzenesulfonyl chloride (2.69 g, 11.0 mmol). After warming to rt and stirring overnight, the mixture was concentrated and the residue was partitioned between CH₂Cl₂ (100 ml) and water (100 ml). The organic layer was washed with brine, dried over NaSO₄, and concentrated. The residue was purified by flash chromatography on silica gel using 10 to 20% EtOAc/hexane gradient, affording the title compound.

Step C: ethyl 3-[4-({[(1Z)-2-tert-butyl-2-methyl-1-oxido-1λ⁵-diazan-1-ylidene]amino}oxy)cyclohexyl]propanoate To a solution of ethyl 3-[4-({[4-(trifluoromethyl)phenyl]sulfonyl}oxy)cyclohexyl]propanoate (3.68 g, 9.01 mmol) in 50 ml DMF was added sodium 1-(N-tert-butylmethylamino)diazen-1-ium-1,2-diolate (3.05 g, 18.02 mmol). After stirring at 45° C. for overnight, the mixture was partitioned between ether (300 ml) and water (300 ml). The organic layer was washed with brine, dried over NaSO₄, and concentrated. The residue was purified by flash chromatography on silica gel using 15% to 40% EtOAc/hexane gradient, affording the title compound.

Step D: 3-[4-({[(1Z)-2-tert-butyl-2-methyl-1-oxido-1λ⁵-diazan-1-ylidene]amino}oxy)cyclohexyl]propanoic acid To the solution of ethyl 3-[4-({[(1Z)-2-tert-butyl-2-methyl-1-oxido-1λ⁵-diazan-1-ylidene]amino}oxy)cyclohexyl]propanoate (570 mg, 1.76 mmol) in ethanol was added NaOH aqueous solution (0.44 ml, 5M). After stirring at rt overnight and concentration, the mixture was partitioned between ether (100 ml) and water (100 ml). The organic layer was washed with brine, dried over NaSO₄, and concentrated. The residue was purified by flash chromatography on silica gel using 30% to 100% EtOAc/hexane gradient, affording the title compound: ¹H NMR (500 MHz, CDCl₃) δ 4.50 (m, 0.6H), 4.21 (m, 0.4H), 2.81 (s, 1.8H), 2.80 (s, 1.2H), 2.37 (t, 2H), 2.17 (m, 1.2H), 2.08 (m, 0.8H), 1.85 (m, 1H), 1.35-1.63 (m, 8H), 1.232 (s, 5.4H) 1.227 (s, 3.6H).

Example 20

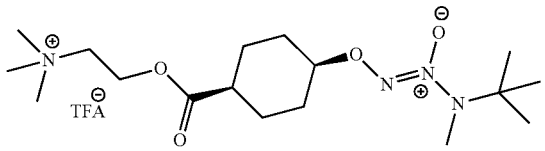 [SMILES: CN(/[N+]([O-])=N/O[C@H]1CC[C@@H](C(=O)OCC[N+](C)(C)C)CC1)C(C)(C)C]

2-({[cis-4-({[(1Z)-2-tert-butyl-2-methyl-1-oxido-1λ⁵-diazan-1-ylidene]amino}oxy)cyclohexyl]carbonyl}oxy)-N,N,N,-trimethylethanaminium trifluoroacetate To a solution of cis-4-({[(1Z)-2-tert-butyl-2-ethyl-1-oxido-1λ⁵-diazan-1-ylidene]amino}oxy)-cyclohexanecarboxylic acid (Example 3, 700 mg, 3.84 mmol) in 10 mL acetonitrile at rt was added choline hydrochloride (536 mg, 3.07 mmol) and followed by HATU (1.169 g, 3.07 mmol), Hunig's base (827 mg, 6.40 mmol). After stirring at rt overnight, the mixture was purified by Waters Mass-Directed Purification System (Waters 30×100 mm Sum Sunfire C18 gradient 90% water with 0.1% TFA/10% MeCN with 0.1% TFA to 0% water/100% MeCN, afford the title compound: ¹H NMR (500 MHz, CDCl₃) 4.56 (m, 2H), 4.55 (m, 1H), 3.71 (m, 2H), 3.22 (s, 9H), 2.79 (s, 3H), 2.56 (m, 1H), 2.00 (m, 2H), 1.80-0.74 (m, 6H), 1.22 (s, 9H).

Example 21

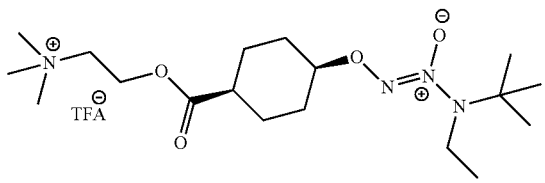 [SMILES: CCN(/[N+]([O-])=N/O[C@H]1CC[C@@H](C(=O)OCC[N+](C)(C)C)CC1)C(C)(C)C]

2-({[cis-4-({[(1Z)-2-tert-butyl-2-ethyl-1-oxido-1λ⁵-diazan-1-ylidene]amino}oxy)cyclohexyl]carbonyl}oxy)-N,N,N-trimethylethanamimum trifluoroacetate The title compound was prepared using procedures described for EXAMPLE 20, substituting trans-4-({[(12)-2-tert-butyl-2-ethyl-1-oxido-1λ⁵-diazan-1-ylidene]amino}oxy)cyclohexanecarboxylic acid (Example 1) for cis-4-({[(1Z)-2-tert-butyl-2-ethyl-1-oxido-1λ⁵-diazan-1-ylidene]amino}oxy)-cyclohexanecarboxylic acid: $^1$H NMR (500 MHz, CDCl$_3$) 4.56 (m, 2H), 4.55 (m, 1H), 3.74 (m, 2H), 3.23 (s, 9H), 3.11 (m, 2H), 2.57 (m, 1H), 2.00 (m, 2H), 1.90-1.74 (m, 6H), 1.21 (s, 9H), 0.98 (t, 3H).

Table 1 shows additional examples that can be prepared following procedures described above:

Activity

Compounds of the invention were evaluated for blood pressure reduction efficacy using the following canine telemetry protocol described below.

Male beagle dogs (approximately 1-3 years old) with a body weight of between 10 and 16 kg were surgically implanted with DSI radiotelemetry devices (model: TL11M2-D70-PCT). Briefly, under an inhalant anesthesia, isoflurane/oxygen mixture (1-3.5%/to effect), the body of the telemetry device was positioned and secured intra-abdominally. Subsequently, the arterial catheter of the telemetry device was passed subcutaneously to the inguinal area and introduced into the femoral artery and advanced to the level of the descending aorta. The catheter was secured with 2-0 silk ligatures. The muscle and underlying fascia was closed over the catheter using absorbable suture and the skin was closed using non-absorbable suture. The animals were allowed a minimum recovery period of 2 weeks between surgery and the evaluation of test compounds.

Compound evaluation consisted of a 3 day paradigm at a 3 mg/kg dose. On the first day, no compounds were administered during a 24 hour period of baseline data collection. Blood pressure and heart rate data were collected continuously for one minute periods at 10 minute intervals. On the days of compound administration half the animals received test article with the other half receiving the vehicle used for

TABLE 1

| Example | |
|---|---|
| 22 | 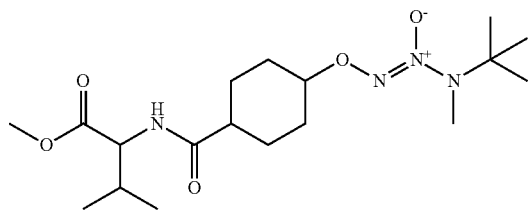 [SMILES: COC(=O)C(NC(=O)C1CCC(O/N=[N+](\[O-])N(C)C(C)(C)C)CC1)C(C)C] |
| 23 | 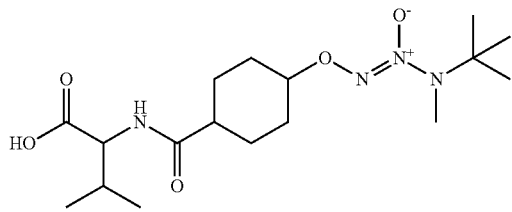 [SMILES: CC(C)C(NC(=O)C1CCC(O/N=[N+](\[O-])N(C)C(C)(C)C)CC1)C(=O)O] |
| 24 | 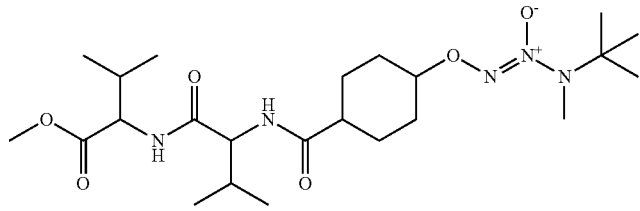 [SMILES: COC(=O)C(NC(=O)C(NC(=O)C1CCC(O/N=[N+](\[O-])N(C)C(C)(C)C)CC1)C(C)C)C(C)C] |
| 25 | 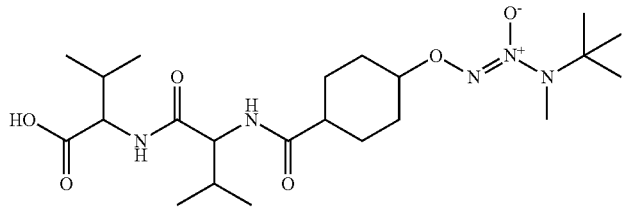 [SMILES: CC(C)C(NC(=O)C(NC(=O)C1CCC(O/N=[N+](\[O-])N(C)C(C)(C)C)CC1)C(C)C)C(=O)O] | compound formulation. All test materials were administered by oral gavage in a volume of 1 mL/kg. Data are expressed either as raw values (mm Hg or beats per minute) or as the change from baseline (average value for about 12 hours in low activity period prior to dosing). Change is SBP (systolic blood pressure) and PP (pulse pressure) over time is shown below:

| Example | ΔSBP (mm Hg) | | | ΔPP (mm Hg) | | |
|---|---|---|---|---|---|---|
| | 1-6 h | 6-12 h | 12-18 h | 1-6 h | 6-12 h | 12-18 h |
| 1 | −9 | −5 | −1 | −1 | −6 | −1 |
| 2 | −14 | −10 | −9 | −9 | −9 | −7 |
| 3 | −8 | −10 | −5 | −7 | −8 | −5 |
| 6 | −18 | −4 | −2 | −12 | −4 | −2 |
| 8 | −14 | −14 | −8 | −11 | −15 | −12 |

What is claimed is:
1. A compound of the formula I:

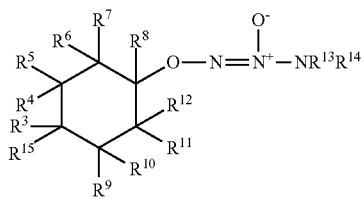

or a pharmaceutically acceptable salt thereof, wherein
$R^3$ is hydrogen, deuterium, —OH, —OC$_{1-6}$alkyl, or halogen;
$R^8$ is hydrogen, deuterium, or —C$_{1-6}$alkyl;
$R^{11}$ and $R^{12}$ are independently hydrogen, —C$_{1-6}$alkyl, —OH, —OC$_{1-6}$alkyl, or halogen;
$R^{13}$ and $R^{14}$ are independently —C$_{1-6}$alkyl, —(CH$_2$)$_{1-2}$OH, or —OC$_{1-6}$alkyl, or, together with the nitrogen atom to which they are attached, form a 4- to 7-membered heterocyclic ring containing one nitrogen atom and 0 or 1 oxygen atoms, wherein said ring is unsubstituted or mono-, di- or tri-substituted with halogen or —C$_{1-6}$alkyl;
—C(O)OCH$_2$CH$_2$N$^+$(CH$_3$)$_3$,
—C(O)NHCH(R$^{17}$)OR$^{16}$, or
—C(O)NHCH(R$^{17}$)C(O)NHCH(R$^{18}$)C(O)OR$^{16}$;
$R^{16}$ is hydrogen, —C$_{1-6}$alkyl, or —(CH$_2$)$_{1-2}$N$^+$R$^{19}$R$^{20}$R$^{21}$; and
$R^1$, $R^2$, $R^4$, $R^5$, $R^6$, $R^7$, $R^9$, $R^{10}$, $R^{17}$, $R^{18}$, $R^{19}$, $R^{20}$, and $R^{21}$ are independently hydrogen or —C$_{1-6}$alkyl.

2. A compound of claim 1, wherein $R^1$ and $R^2$ are hydrogen, or a pharmaceutically acceptable salt thereof.

3. A compound of claim 1, wherein $R^3$ is hydrogen or deuterium, or a pharmaceutically acceptable salt thereof.

4. A compound of claim 1, wherein $R^5$ is hydrogen or methyl, or a pharmaceutically acceptable salt thereof.

5. A compound of claim 1, wherein $R^4$, $R^6$, $R^7$, $R^8$, $R^9$, and $R^{10}$, are hydrogen, or a pharmaceutically acceptable salt thereof.

6. A compound of claim 1, wherein $R^{13}$ is —CH$_3$, —CH$_2$CH$_3$, —CH$_2$CH$_2$CH$_2$CH$_3$, or —CH$_2$CH$_2$OH, or a pharmaceutically acceptable salt thereof.

7. A compound of claim 1, wherein $R^{14}$ is —CH(CH$_3$)$_2$, —CH$_2$CH$_3$, or —C(CH$_3$)$_3$, or a pharmaceutically acceptable salt thereof.

8. A compound of claim 1, wherein $R^{15}$ is —C(O)OH, or a pharmaceutically acceptable salt thereof.

9. A compound of claim 1, wherein $R^{15}$ is —C(O)OCH$_2$CH$_2$N$^+$(CH$_3$)$_3$, or a pharmaceutically acceptable salt thereof.

10. A compound of claim 1, wherein $R^{15}$ is —C(O)NHCH(CH(CH$_3$)$_2$)OR$^{16}$, or —C(O)NHCH(CH(CH$_3$)$_2$)C(O)NHCH(CH(CH$_3$)$_2$)C(O)OR$^{16}$, and wherein $R^{16}$ is hydrogen or —CH$_3$, or a pharmaceutically acceptable salt thereof.

11. A compound of claim 1, which is
Cis-4-({[(1Z)-2-tert-butyl-2-ethyl-1-oxido-1λ$^5$-diazan-1-ylidene]amino}oxy)-cyclohexanecarboxylic acid,
Trans-4-({[(1Z)-2-tert-butyl-2-ethyl-1-oxido-1λ$^5$-diazan-1-ylidene]amino}oxy)-cyclohexanecarboxylic acid,
Cis-4-({[(1Z)-2-tert-butyl-2-methyl-1-oxido-1λ$^5$-diazan-1-ylidene]amino}oxy)-cyclohexanecarboxylic acid,
Cis-4-({[(1Z)-2-butyl-2-tert-butyl-1-oxido-1λ$^5$-diazan-1-ylidene]amino}oxy)-cyclohexanecarboxylic acid,
Cis-4-({[(1Z)-2-methyl-1-oxido-(2-propan-2-yl)-1λ$^5$-diazan-1-ylidene]amino}oxy)-cyclohexanecarboxylic acid,
Trans-4-({[(1Z)-2-tert-butyl-2-methyl-1-oxido-1λ$^5$-diazan-1-ylidene]amino}oxy)-cyclohexanecarboxylic acid,
Trans-4-({[(1Z)-2-tert-butyl-2-(2-hydroxyethyl)-1-oxido-1λ$^5$-diazan-1-ylidene]amino}oxy)-cyclohexanecarboxylic acid,
Trans-4-({[(1Z)-2-butyl-2-tert-butyl-1-oxido-1λ$^5$-diazan-1-ylidene]amino}oxy)-cyclohexanecarboxylic acid,
Trans-4-({[(1Z)-2-methyl-1-oxido-(2-propan-2-yl)-1λ$^5$-diazan-1-ylidene]amino}oxy)-cyclohexanecarboxylic acid,
Trans-4-({[(1Z)-2,2-diethyl-1-oxido-1λ$^5$-diazan-1-ylidene]amino}oxy)-cyclohexanecarboxylic acid,
Cis-4-({[(1Z)-2-tert-butyl-2-methyl-1-oxido-1λ$^5$-diazan-1-ylidene]amino}oxy)(1-$^2$H)cyclohexanecarboxylic acid,
Trans-4-({[(1Z)-2-tert-butyl-2-methyl-1-oxido-1λ$^5$-diazan-1-ylidene]amino}oxy)(1-$^2$H)cyclohexanecarboxylic acid,
(1RS,2SR,4RS)-4-({[(1Z)-2-tert-butyl-2-methyl-1-oxido-1λ$^5$-diazan-1-ylidene]amino}oxy)-2-methylcyclohexanecarboxylic acid,
(1RS,2SR,4RS)-4-({[(1Z)-2-tert-butyl-2-methyl-1-oxido-1λ$^5$-diazan-1-ylidene]amino}oxy)-2-methylcyclohexanecarboxylic acid,
(1RS,2RS,4RS)-4-({[(1Z)-2-tert-butyl-2-methyl-1-oxido-1λ$^5$-diazan-1-ylidene]amino}oxy)-2-methylcyclohexanecarboxylic acid,
(1RS,2RS,4RS)-4-({[(1Z)-2-tert-butyl-2-methyl-1-oxido-1λ$^5$-diazan-1-ylidene]amino}oxy)-2-methylcyclohexanecarboxylic acid,
(1RS,3SR)-3-({[(1Z)-2-tert-butyl-2-methyl-1-oxido-1λ$^5$-diazan-1-ylidene]amino}oxy)cyclohexanecarboxylic acid,
[4-{([(1Z)-2-tert-butyl-2-methyl-1-oxido-1λ$^5$-diazan-1-ylidene]amino}oxy)cyclohexyl]acetic acid,
3-[4-({[(1Z)-2-tert-butyl-2-methyl-1-oxido-1λ$^5$-diazan-1-ylidene]amino}oxy)cyclohexyl]propanoic acid,
2-({[cis-4-({[(1Z)-2-tert-butyl-2-methyl-1-oxido-1λ$^5$-diazan-1-ylidene]amino}oxy)cyclohexyl]carbonyl}oxy)-N,N,N-trimethylethanaminium trifluoroacetate,
2-({[cis-4-({[(1Z)-2-tert-butyl-2-ethyl-1-oxido-1λ$^5$-diazan-1-ylidene]amino}oxy)cyclohexyl]carbonyl}oxy)-N,N,N-trimethylethanaminium trifluoroacetate,
or a pharmaceutically acceptable salt thereof.

12. A pharmaceutical composition comprising a compound of claim 1 and a pharmaceutically acceptable carrier.

13. A pharmaceutical composition comprising a compound of claim 11 and a pharmaceutically acceptable carrier.

14. A pharmaceutical composition comprising a compound of claim 11, a diuretic, and a pharmaceutically acceptable carrier.

15. A method for treating hypertension in a patient which comprises administering to the patient a therapeutically effective amount of the composition of claim 13.

* * * * *